United States Patent
Oggianu et al.

(10) Patent No.: US 12,241,878 B2
(45) Date of Patent: Mar. 4, 2025

(54) GAS DETECTOR TEST AND CALIBRATION METHOD AND APPARATUS

(71) Applicant: Carrier Corporation, Palm Beach Gardens, FL (US)

(72) Inventors: Stella M. Oggianu, Farmington, CT (US); Jason R. Kondrk, Clay, NY (US); Paul V. Weyna, Manilus, NY (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 204 days.

(21) Appl. No.: 15/734,224

(22) PCT Filed: May 13, 2020

(86) PCT No.: PCT/US2020/032634
§ 371 (c)(1),
(2) Date: Dec. 1, 2020

(87) PCT Pub. No.: WO2020/236480
PCT Pub. Date: Nov. 26, 2020

(65) Prior Publication Data
US 2022/0065832 A1    Mar. 3, 2022

Related U.S. Application Data (60) Provisional application No. 62/993,916, filed on Mar. 24, 2020, provisional application No. 62/849,324, filed on May 17, 2019.

(51) Int. Cl.
G01N 33/00 (2006.01)
B60H 1/00 (2006.01)
F25D 29/00 (2006.01)

(52) U.S. Cl.
CPC ..... *G01N 33/0006* (2013.01); *B60H 1/00585* (2013.01); *B60H 1/008* (2013.01); *F25D 29/003* (2013.01); *F25D 29/006* (2013.01)

(58) Field of Classification Search
CPC .......... G01N 33/0006; G01N 27/4175; G01N 21/274; B60H 1/00585; B60H 1/00792; B60H 1/008; F25D 29/003; F25D 29/006
(Continued)

(56) References Cited

U.S. PATENT DOCUMENTS 3,295,724 A * 1/1967 Brooks ................ B01F 23/235
222/399
4,305,724 A * 12/1981 Micko .................... G01N 27/16
73/23.31
(Continued)

FOREIGN PATENT DOCUMENTS

CN    105424888 A      3/2016
CN    105866331 A  *   8/2016   ......... G01N 33/0006
(Continued)

OTHER PUBLICATIONS

Espacenet Machine Translation of JP 2017-044577 A Which Originally Published On Mar. 2, 2017. (Year: 2017).*
(Continued)

*Primary Examiner* — Patrick Assouad
*Assistant Examiner* — Nashmiya S Fayyaz
(74) *Attorney, Agent, or Firm* — CANTOR COLBURN LLP (57) ABSTRACT

A detector testing system for testing a gas detector used in a heating, ventilation, and air conditioning, or refrigeration (HVAC\R) system including: a testing chamber configured to receive the gas detector through an orifice in the detector testing system, the testing chamber being configured to at least partially enclose the gas detector within the testing
(Continued)

chamber; a receiving port fluidly connected to the testing chamber; and a target gas cartridge fluidly connected to the receiving port, wherein the target gas cartridge contains a known concentration of a target gas, wherein the receiving port is configured to deliver the target gas to the testing chamber.

9 Claims, 5 Drawing Sheets

(58) Field of Classification Search
USPC .................................................. 73/1.02, 1.06
See application file for complete search history.

(56) References Cited

U.S. PATENT DOCUMENTS

| | | | | |
|---|---|---|---|---|
| 4,489,590 | A * | 12/1984 | Hadden | G01N 33/0006 73/1.04 |
| 4,591,093 | A | 5/1986 | Elliott, Jr. | |
| 4,700,560 | A * | 10/1987 | Hoffa | G01N 33/0006 73/864.83 |
| 4,882,576 | A | 11/1989 | Boyd | |
| 5,071,768 | A | 12/1991 | Klodowski | |
| 5,174,124 | A | 12/1992 | Paige et al. | |
| 5,207,087 | A * | 5/1993 | Costello | A61B 5/1495 73/1.02 |
| 5,255,527 | A | 10/1993 | Paige | |
| 5,343,747 | A * | 9/1994 | Rosen | G01N 25/56 165/223 |
| 5,371,019 | A | 12/1994 | Manz et al. | |
| 5,514,595 | A | 5/1996 | Olds et al. | |
| 5,670,946 | A * | 9/1997 | Ellwood | G08B 29/145 340/630 |
| 5,783,110 | A * | 7/1998 | Verdicchio | B01J 13/0052 252/189 |
| 6,237,392 | B1 | 5/2001 | Yu et al. | |
| 6,741,181 | B2 * | 5/2004 | Skaggs | G08B 17/113 73/40.5 R |
| 6,742,384 | B2 | 6/2004 | Avila | |
| 6,772,598 | B1 | 8/2004 | Rinehart | |
| 7,073,368 | B2 | 7/2006 | Wood et al. | |
| 7,107,821 | B2 * | 9/2006 | Bohm | G01M 3/207 73/40 |
| 7,146,841 | B2 | 12/2006 | Forrest | |
| 7,168,287 | B2 * | 1/2007 | Rolff | G01M 3/207 73/1.05 |
| 7,275,411 | B2 | 10/2007 | Peng | |
| 7,281,405 | B2 * | 10/2007 | Mayer | G01N 33/54373 73/1.06 |
| 7,383,158 | B2 | 6/2008 | Krocker et al. | |
| 7,444,854 | B2 * | 11/2008 | Bohm | G01M 3/207 73/1.05 |
| 7,587,926 | B2 * | 9/2009 | Ackerman | B65D 83/30 73/1.02 |
| 7,655,186 | B2 | 2/2010 | Tobias | |
| 7,661,290 | B2 | 2/2010 | Gu et al. | |
| 7,716,962 | B2 | 5/2010 | Woodford et al. | |
| 7,730,759 | B2 * | 6/2010 | Rombach | G01N 25/56 73/1.61 |
| 7,975,525 | B2 | 7/2011 | Bonne et al. | |
| 8,117,886 | B2 * | 2/2012 | Rolff | G01M 3/207 73/40 |
| 8,364,431 | B2 | 1/2013 | Russell et al. | |
| 8,701,458 | B2 * | 4/2014 | Emtell | G01N 33/0006 73/1.06 |
| 8,869,585 | B2 * | 10/2014 | Troughton | A61B 5/1495 73/1.88 |
| 9,064,386 | B2 * | 6/2015 | Won | G08B 3/00 |
| 9,110,041 | B2 * | 8/2015 | Flanders | G01N 33/0006 |
| 9,255,917 | B2 * | 2/2016 | Miyai | G01N 33/0006 |
| 9,518,966 | B2 | 12/2016 | Duric et al. | |
| 9,945,826 | B2 * | 4/2018 | Oberlin | G01N 25/18 |
| 10,101,298 | B1 | 10/2018 | Zhang et al. | |
| 10,527,597 | B2 * | 1/2020 | Krauss | G01N 33/0006 |
| 2004/0139787 | A1 * | 7/2004 | Bohm | G01M 3/207 73/40 |
| 2006/0016249 | A1 * | 1/2006 | Ache | G01M 3/228 73/40.7 |
| 2006/0101925 | A1 | 5/2006 | Peng et al. | |
| 2010/0326165 | A1 | 12/2010 | Rauworth et al. | |
| 2013/0245965 | A1 | 9/2013 | Kane et al. | |
| 2014/0091939 | A1 | 4/2014 | Won et al. | |
| 2016/0363358 | A1 * | 12/2016 | Papas | F25B 49/005 |
| 2016/0370334 | A1 | 12/2016 | Van Tol | |
| 2017/0059185 | A1 * | 3/2017 | Suzuki | F25B 47/025 |
| 2017/0350616 | A1 * | 12/2017 | Yenni | F24F 11/30 |
| 2018/0259479 | A1 | 9/2018 | Yoshikawa et al. | |
| 2018/0267003 | A1 | 9/2018 | Johnson et al. | |
| 2019/0025154 | A1 * | 1/2019 | Johnson | G01M 3/38 |
| 2019/0033220 | A1 | 1/2019 | Staats et al. | |
| 2019/0195542 | A1 * | 6/2019 | Hansen | F24F 1/32 |
| 2020/0363383 | A1 * | 11/2020 | Chow | G01N 33/0006 |
| 2021/0095887 | A1 * | 4/2021 | Kilgo | F24F 11/36 |

FOREIGN PATENT DOCUMENTS

| | | | | |
|---|---|---|---|---|
| CN | 206248631 | U | * | 6/2017 |
| CN | 207280683 | U | | 4/2018 |
| CN | 109470743 | A | * | 3/2019 |
| EP | 2293267 | A1 | | 3/2011 |
| EP | 3109635 | A1 | | 12/2016 |
| GB | 2345340 | A | | 7/2000 |
| JP | 2015534190 | A | | 11/2015 |
| JP | 2017044577 | A | * | 3/2017 |
| JP | 2018124180 | A | | 8/2018 |
| KR | 20140071582 | A | * | 6/2014 |
| WO | 2015043796 | A1 | | 4/2015 |
| WO | WO-2017083336 | A1 | * | 5/2017 ................ B60P 3/20 |

OTHER PUBLICATIONS

Internation Search Report; International Application No. PCT/US2020/032634; International Filing Date: May 13, 2020; Date of Mailing: Sep. 8, 2020; pp. 1-6.
ISR Written Opinion; International Application No. PCT/US2020/032634; International Filing Date: May 13, 2020; Date of Mailing: Sep. 8, 2020; pp. 1-9.
Japanese Office Action for Application No. JP2020571807; Issued Nov. 21, 2023, 8 Pages.
Chinese Office Action for Application No. 202080003577.1, Mar. 29, 2024, 10 Pages.
Japanese Office Action for Application No. JP2020571807; Issued Mar. 5, 2024, 8 Pages.

* cited by examiner

GAS DETECTOR TEST AND CALIBRATION METHOD AND APPARATUS

CROSS REFERENCE TO RELATED APPLICATIONS

This application is a National Stage application of PCT/US2020/032634, filed May 13, 2020, which claims the benefit of U.S. Provisional Patent Application No. 62/993,916, filed Mar. 24, 2020 and U.S. Provisional Patent Application No. 62/849,324, filed May 17, 2019, all of which are incorporated by reference in their entirety herein.

BACKGROUND

The subject matter disclosed herein generally relates to the gas sensing, and more particularly to an apparatus and method for testing gas sensors and detection systems.

Products may be shipped or stored within a conditioned space, such as a container, truck or trailer. These conditioned spaces utilize a refrigeration unit that circulates cooled air inside the interior volume. In many cases, the refrigeration unit uses a refrigeration cycle to cool the air. Refrigerant from the refrigeration unit may leak and thus it needs to be verified that gas detection systems are operating correctly to successfully detect the leak.

BRIEF SUMMARY

According to one embodiment, a detector testing system for testing a gas detector used in a heating, ventilation, and air conditioning, or refrigeration (HVAC\R) system. The detector testing system including: a testing chamber configured to receive the gas detector through an orifice in the detector testing system, the testing chamber being configured to at least partially enclose the gas detector within the testing chamber; a receiving port fluidly connected to the testing chamber; and a target gas cartridge fluidly connected to the receiving port, wherein the target gas cartridge contains a known concentration of a target gas, wherein the receiving port is configured to deliver the target gas to the testing chamber.

In addition to one or more of the features described above, or as an alternative, further embodiments may include a door configured to seal against the orifice and fully enclose the gas detector within the testing chamber.

In addition to one or more of the features described above, or as an alternative, further embodiments may include that the orifice is configured to seal against a mounting surface of the HVAC/R system and enclose the gas detector within the testing chamber.

In addition to one or more of the features described above, or as an alternative, further embodiments may include a communication device in electronic communication with a communication device of the gas detector.

In addition to one or more of the features described above, or as an alternative, further embodiments may include a display device configured to display detector readings detected by the gas detector.

In addition to one or more of the features described above, or as an alternative, further embodiments may include that the target gas is a refrigerant.

In addition to one or more of the features described above, or as an alternative, further embodiments may include that the target gas is a mildly flammable refrigerant.

In addition to one or more of the features described above, or as an alternative, further embodiments may include that the target gas is an A2 refrigerant, A2L refrigerant, or an A3 refrigerant.

In addition to one or more of the features described above, or as an alternative, further embodiments may include that the known concentration of the target gas within the target gas cartridge is a lower flammability limit of the target gas.

In addition to one or more of the features described above, or as an alternative, further embodiments may include that the target gas within the target gas cartridge is diluted to a lower flammability limit of the target gas prior to the target gas entering the testing chamber.

In addition to one or more of the features described above, or as an alternative, further embodiments may include: an environmental control configured to adjust an environmental conditions within the testing chamber; and an environmental sensor configured to detect the environmental condition within the testing chamber.

In addition to one or more of the features described above, or as an alternative, further embodiments may include that the environmental condition.

In addition to one or more of the features described above, or as an alternative, further embodiments may include: a communication device in electronic communication with a communication device of the gas detector, wherein the communication device is configured to received readings detected by the gas detector and transmit the readings to a cloud server.

In addition to one or more of the features described above, or as an alternative, further embodiments may include a communication device in electronic communication with a communication device of the gas detector, wherein the communication device is configured to communicate with the gas detector for recalibration of the gas detector.

According to another embodiment, a method of testing a gas detector for a heating, ventilation, and air conditioning, or refrigeration (HVAC/R) system is provided. The method including: inserting the gas detector through an orifice in a detector testing system and at least partially into a testing chamber within the detector testing system, the testing chamber being configured to at least partially enclose the gas detector within the testing chamber; sealing the testing chamber off from external environments; providing a target gas into the testing chamber; and receiving one or more readings from HVAC/R system.

In addition to one or more of the features described above, or as an alternative, further embodiments may include that sealing the testing chamber off from external environments further includes: removing the gas detector from the HVAC/R system; inserting the gas detector fully into the testing chamber; and closing a door of the testing chamber, the door being configured to seal against the orifice and fully enclose the gas detector within the testing chamber.

In addition to one or more of the features described above, or as an alternative, further embodiments may include that sealing the testing chamber off from external environments further includes: sealing the orifice against a mounting surface of the HVAC/R system, the gas detector remaining attached to the mounting surface; and enclosing the gas detector within the testing chamber.

In addition to one or more of the features described above, or as an alternative, further embodiments may include: displaying the one or more detector readings detected by the gas detector within the detector testing system.

In addition to one or more of the features described above, or as an alternative, further embodiments may include that the target gas is a refrigerant.

In addition to one or more of the features described above, or as an alternative, further embodiments may include that the target gas is a flammable refrigerant.

In addition to one or more of the features described above, or as an alternative, further embodiments may include that the target gas is an A2 refrigerant, A2L refrigerant, or an A3 refrigerant.

In addition to one or more of the features described above, or as an alternative, further embodiments may include that prior to providing the target gas into the testing chamber, the method further includes: diluting the target gas to a lower flammability limit of the target gas prior to the target gas entering the testing chamber.

In addition to one or more of the features described above, or as an alternative, further embodiments may include: detecting an environmental condition within the testing chamber using an environmental sensor; and adjusting the environmental condition within the testing chamber using an environmental control.

In addition to one or more of the features described above, or as an alternative, further embodiments may include that receiving readings from the gas detector; and transmitting the readings to a cloud server.

In addition to one or more of the features described above, or as an alternative, further embodiments may include: receiving readings from the gas detector; determining a recalibration of the gas detector is required in response to the readings; and transmitting the calibration parameters or adjustments for recalibration of the gas detector to the gas detector.

In addition to one or more of the features described above, or as an alternative, further embodiments may include: receiving response data from the HVAC/R system; and determining whether the HVAC/R system has performed or is performing an isolation and pump down procedure following the introduction of the target gas into the testing chamber.

In addition to one or more of the features described above, or as an alternative, further embodiments may include: transporting the target gas from the testing chamber to a target gas tank.

According another embodiment, detector testing system for testing a gas detector used in a heating, ventilation, and air conditioning, or refrigeration (HVAC\R) system is provided. The detector testing system including: a testing cup having a cup mounting surface with an orifice; a testing chamber extending from the orifice of the cup mounting surface into the testing cup; a target gas delivery hose fluidly connected to the testing chamber; and a target gas tank fluidly connected to the testing chamber through the target gas delivery hose, wherein the target gas delivery hose is configured to deliver a target gas from the target gas tank to the testing chamber.

In addition to one or more of the features described above, or as an alternative, further embodiments may include that the cup mounting surface is configured to seal against a mounting surface of the HVAC/R system and enclose the gas detector within the testing chamber.

In addition to one or more of the features described above, or as an alternative, further embodiments may include that the target gas is a refrigerant.

In addition to one or more of the features described above, or as an alternative, further embodiments may include that the target gas is a mildly flammable refrigerant.

In addition to one or more of the features described above, or as an alternative, further embodiments may include that the target gas is an A2 refrigerant, A2L refrigerant, or an A3 refrigerant.

In addition to one or more of the features described above, or as an alternative, further embodiments may include: a target gas metering component located within the target gas delivery hose interposed between the testing chamber and the target gas tank.

In addition to one or more of the features described above, or as an alternative, further embodiments may include: a target gas return hose fluidly connecting the testing chamber to the target gas tank; and a target gas reclaim component located within the target gas return hose interposed between the testing chamber and the target gas tank.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
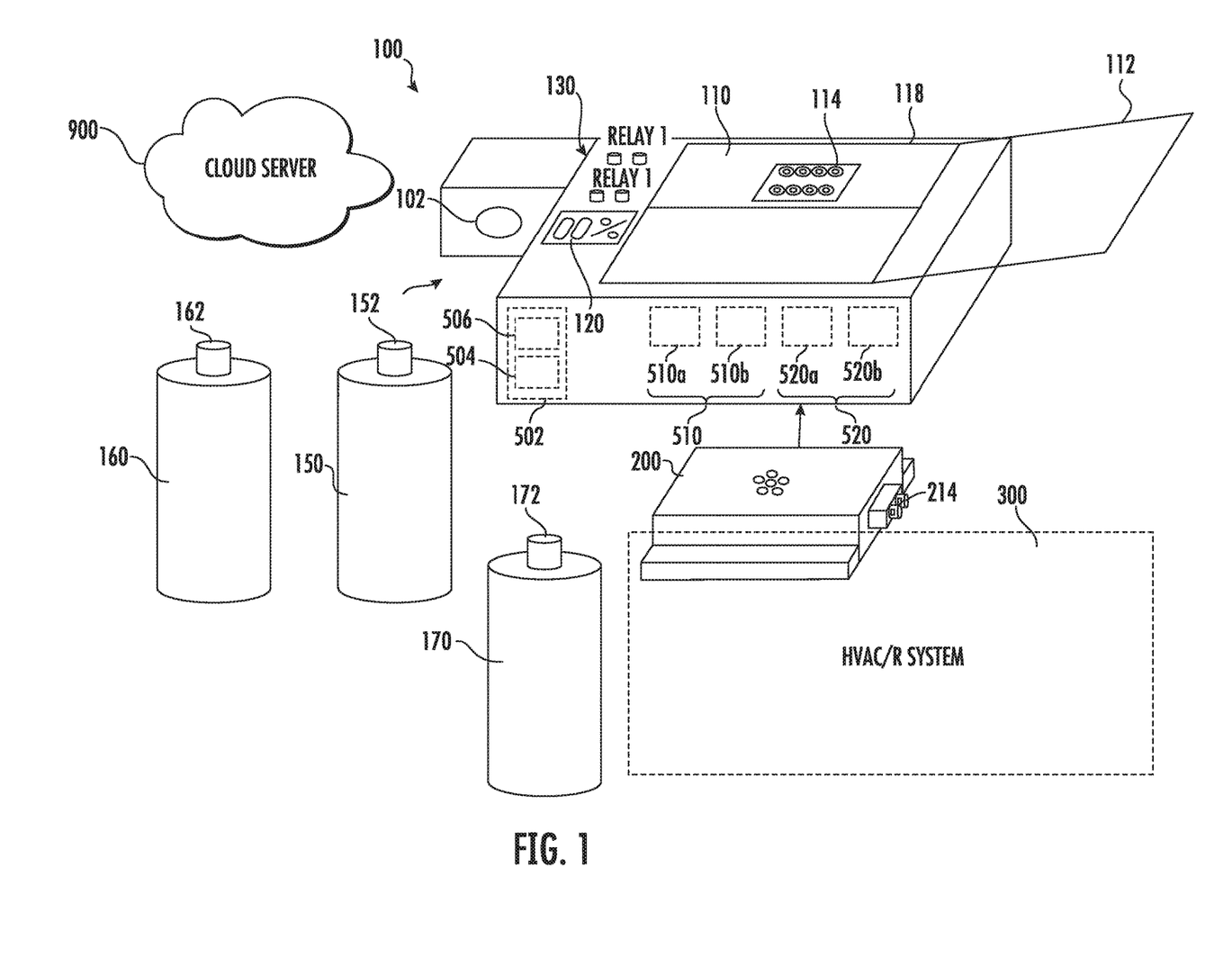
FIG. 1 illustrates a general system diagram of a detector testing system, in accordance with an embodiment of the disclosure.
Figure 2:
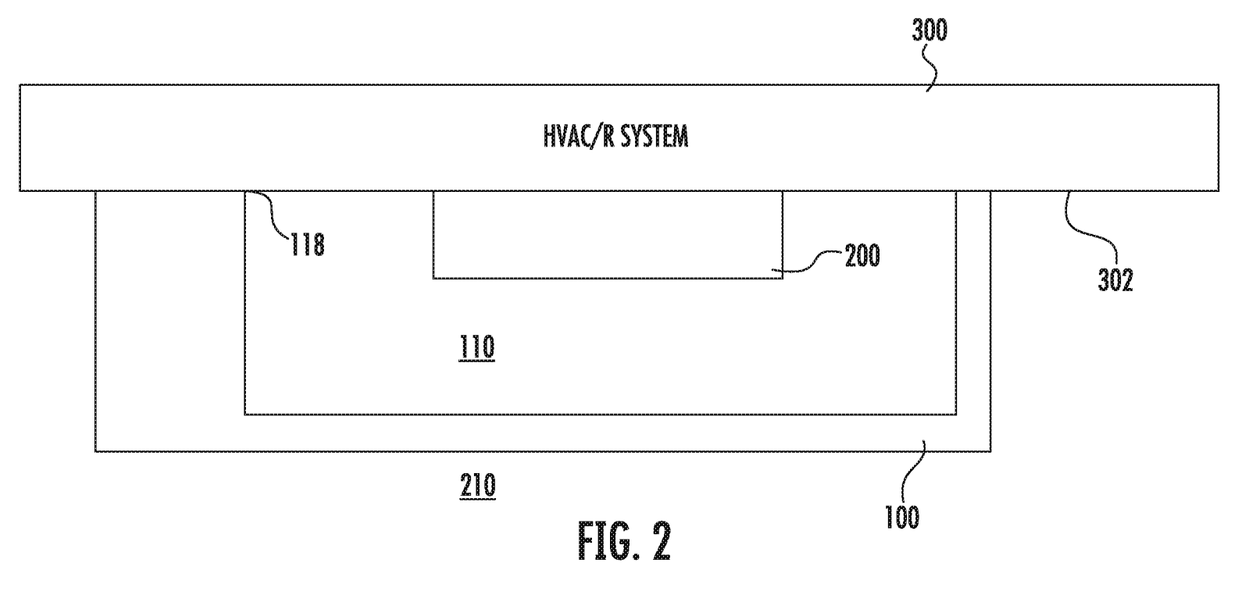
FIG. 2 illustrates a gas detector within a detector testing system, in accordance with an embodiment of the disclosure.

FIGS. 1-2 schematically illustrates a detector testing system 100 configured to test a gas detector 200. The gas detector 200 may contain various components that are tested by the detector testing system 100, such as for example gas sensors, diagnostic algorithms, and mitigation mechanisms such as lights, relays and switches. It should be appreciated that, although particular systems are separately defined in the schematic block diagrams, each or any of the systems may be otherwise combined or separated via hardware and/or software. The gas detector 200 may be used in a heating, ventilation, and air conditioning or refrigeration (HVAC/R) system 300 to detect a target gas. In an embodiment, the target gas is a refrigerant. In an embodiment, the target gas is a flammable and/or a mildly flammable refrigerant. In one embodiment, a mildly flammable refrigerant may be defined as a refrigerant having a greater than 0.3 kg/m$^3$, a heat of combustion less than 19,000 kj/kg, and/or a burning velocity of less than 10 cm/s. In an embodiment, the mildly flammable refrigerant may be A2L refrigerant. An A2L refrigerant may include but is not limited to R32, R1234yf, R-1234ze(E), R134A, R454A, and R454B. In another embodiment, the target gas may be a higher flammability refrigerant, such as, for example an A3 refrigerant. In another embodiment, the target gas is an A2 refrigerant, A2L refrigerant, or an A3 refrigerant. An A2 refrigerant may include but is not limited to R-152a. An A3 refrigerant may include but is not limited to R-290 (Propane) and R-600a (isobutene).

The HVAC/R system 300 may be a commercial or residential stationary HVAC system or a transport or stationary refrigeration (R) system. The gas detector 200 may be utilized in operative association with a transport HVAC/R system, such as, for example, a refrigerated truck, a refrigerated trailer, or a refrigerated container. The gas detector 200 may also be utilized in operative association with a stationary HVAC/R system, such as, for example, refrigerated cabinets (e.g., self-serve refrigerated grocery cabinets with and without doors). In the transport refrigeration system or the commercial refrigeration system, the gas detector 200 may be used as part of a refrigeration control system to adjust environmental conditions of the perishable goods (e.g., cargo/stock/inventory) in order to control or influence the control of ventilation, humidity, air temperature, and/or contaminant scrubbing systems. In one embodiment, the gas detector 200 may be used to activate ventilation to lower the target gas concentration around the gas detector 200, or to alert personnel to the presence of the target gas, or potential damage to property or perishable goods. In another embodiment, the gas detector 200 may be utilized independent of a corresponding refrigeration system or commercial refrigeration system to alert personnel to potential damage to perishable goods, alert personnel to the presence of the target gas, and/or to increase or decrease ventilation rates.

The detector testing system 100 may be separate and apart from the gas detector 200 and may be utilized to test the gas detector 200 periodically or intermittently, as required. The detector testing system 100 may be brought onsite to test the gas detector 200. The gas detector 200 may be removed from the HVAC/R system 300 and tested within the detector testing system 100 or the detector testing system 100 may be brought to the HVAC/R system 300 to test the gas detector 200 while remaining installed in the HVAC/R system 300, as described herein.

The detector testing system 100 includes a testing chamber 110 capable of fully and/or partially enclosing the gas detector 200. In the embodiment illustrated in FIG. 1, the gas detector 200 is removed from the HVAC/R system 300 and tested within the detector testing system 100, which fully encloses the gas detector 200. The gas detector 200 may be removed from the HVAC/R system 300 and placed within the testing chamber 110. The detector testing system 100 may include a door 112 to environmentally seal the testing chamber 110 from external environments 210, thus creating a controlled environment within the testing chamber 110. The door 112 is configured to seal against an orifice 118 of the detector testing system 100, which opens up into the testing chamber 110.

In the embodiment illustrated in FIG. 2, the gas detector 200 is not removed from a mounting surface 302 of the HVAC/R system 300 and tested within the detector testing system 100 while still being mounted to the mounting surface 302. As shown in FIG. 2, the gas detector 200 is inserted into an orifice 118 of the detector testing system 100. The orifice 118 opens up into the testing chamber 110. The orifice 118 is configured to seal against the mounting surface 302 of the HVAC/R system 300, while the testing chamber 110 encloses the gas detector 200. The orifice 118 sealing against the mounting surface 302 of the HVAC/R system 300 environmentally seals (i.e., isolates) the gas detector 200 within the testing chamber 110 and prevents gas leakage between the testing chamber 110 and an external environment 210 outside of the testing chamber 110.

When the gas detector 200 is sealed within the testing chamber 110, the detector testing system 100 is configured to emit a known concentration of the target gas into the testing chamber 110 to test a state of health of the gas detector 200. The detector testing system 100 may be in wired and/or wireless communication with the gas detector 200 when the gas detector 200 is located within the testing chamber 110 to receive detector readings from the gas detector 200. The detector testing system 100 may include a communication device 114 and the gas detector 200 may include a communication device 114. In one embodiment, the communication device 214 of the gas detector 200 may be hardwired to the communication device 114 of the detector testing system 100 through a removable connecting wire (not shown). In another embodiment, the communication device 214 of the gas detector 200 may be in wireless communication with the communication device 114 of the detector testing system 100 through a short-range wireless transmissions, such as, for example, Bluetooth, Wi-Fi, Infrared, etc.

In one embodiment, a memory 506 of a controller 502 of the detector testing system 100 or any other memory device within the detector testing system 100 may be utilized to locally store testing data, including, but not limited to, building name, building number, room number, HVAC/R identification number, station number, time, test number, target gas name, target gas concentration, detector name, detector location, detector baseline, readings from the gas detector 200, detector response as function of time, the known concentration of the target gas within the target gas cartridge 150, the concentration of target gas delivered into the testing chamber 110, the humidity within the testing chamber 110, and the temperature within the testing chamber 110, and the like.

In one embodiment, the controller 502 of the detector testing system 100 may be configured to locally analyze the testing data, determine a pass or fail decision for the gas detector 200, and display the pass or fail decision back on the detector testing system 100.

In another embodiment, the communication device 214 of the gas detector 200 may be in wireless communication with a cloud server 900 through a wireless transmissions, such as, for example, Bluetooth, Wi-Fi, Infrared, cellular, satellite, or other network communication. The communication device 214 may be configured to transmit the testing data to the cloud server 900. The cloud server 900 may be configured to analyze the testing data, determine a pass or fail decision for the gas detector 200, and transmit the pass or fail decision back to the detector testing system 100 for local display.

In another embodiment, the communication device 214 of the gas detector 200 may be in wired communication with another device, such as, for example, for example a phone, a laptop. In addition to determining a pass or fail, the controller 502 and/or the cloud server 900 may alternatively determine that the gas detector 200 needs to be recalibrated using the detector testing system 100. The communication device 114 of the detector testing system 100 may be in wireless communication with the communication device 214 of the gas detector 200 through a short-range wireless transmissions, such as, for example, Bluetooth, Wi-Fi, Infrared, etc. The communication device 114 of the detector testing system 100 may be in wired communication with the communication device 214 of the gas detector 200 through a USB cable, Ethernet, fiber-optics, etc. Through the communication devices 114, 214, the detector testing system 100 may be able to pass to the gas detector 200 calibration parameters or adjustments thereto for recalibration of the gas detector 200, which may be an automatic process. For example, once connected with the gas detector 200, the detector testing system 100 can pair with the gas detector 200 to start a calibration test where it delivers a known concentration of target gas into the testing chamber 110. Upon receiving the readings from the gas detector 200 in response to the target gas then the detector testing system 100 can send updated calibration parameters to the gas detector 200 and then rerun the test to confirm that the gas detector 200 has been successfully recalibrated. This recalibration process can be done at various temperature levels and humidity levels as discussed herein.

The controller 502 may be configured to control entry of the target gas into the testing chamber 110. The controller 502 may be an electronic controller including a processor 504 and an associated memory 506 comprising computer-executable instructions that, when executed by the processor 504, cause the processor 504 to perform various operations. The processor 504 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 506 may be but is not limited to a random access memory (RAM), read only memory (ROM), or other electronic, optical, magnetic or any other computer readable medium.

The target gas may be received from a target gas cartridge 150. The target gas cartridge 150 may include an output port 152 that fluidly connects to a receiving port 102 of the detector testing system 100. The receiving port 102 is fluidly connected to the testing chamber 110 and configured to deliver the target gas into the testing chamber 110. The target gas cartridge 150 contains a known concentration of the target gas, such as, for example, 0%, 10%, 20%, 30%, 40%, 50%, 60%, 70%, 80%, 90%, 100%, or any concentration therebetween. In one embodiment, the target gas cartridge 150 may contain a known concentration of the target gas equal to 100% and the detector testing system 100 may include a flow meter to adjust flow of the target gas from the target gas cartridge 150 into the testing chamber 110.

Although only one is shown, the detector testing system 100 may include multiple receiving ports 102 that connect to multiple target gas cartridges 150 and/or a dilution gas cartridge 160. In the event multiple target gas cartridges 150 are utilized, each of the multiple target gas cartridges 150 may contain a different known concentration of the target gas. The dilution gas cartridge 160 may also include an output port 162 that fluidly connects to a receiving port 102 of the detector testing system 100. In an embodiment, the detector testing system 100 may include a flow meter to help dilute the target gas. The flow meter is not shown for simplification of illustration.

In one embodiment, the detector testing system 100 may introduce the target gas from the target gas cartridge 150 directly into the testing chamber 110 without diluting the target gas received from the target gas cartridge 150. In another embodiment, the detector testing system 100 may dilute the target gas received from the target gas cartridge 150 prior to entering into the testing chamber 110 using external air or a gas from the dilution gas cartridge 160. In an embodiment, the known concentration of the target gas within the target gas cartridge 150 is a lower flammability limit (LFL) of the target gas. In another embodiment, the known concentration of the target gas within the target gas cartridge 150 may be diluted to the LFL of the target gas prior to entering the testing chamber 110.

The detector testing system 100 may also be configured to test a responsiveness of the gas detector 200 to a non-target gas. The non-target gas may be received from a non-target gas cartridge 170. The non-target gas cartridge 170 may include an output port 172 that fluidly connects to a receiving port 102 of the detector testing system 100. The non-target gas cartridge 170 contains a known concentration of a non-target gas, such as, for example, 0%, 10%, 20%, 30%, 40%, 50%, 60%, 70%, 80%, 90%, 100%, or any concentration therebetween. In one embodiment, the detector testing system 100 may introduce the non-target gas from the non-target gas cartridge 170 directly into the testing chamber 110 without diluting the non-target gas received from the non-target gas cartridge 170. In another embodiment, the detector testing system 100 may dilute the non-target gas received from the non-target gas cartridge 170 prior to entering into the testing chamber 110 using external air or a gas from a dilution gas cartridge 160. Advantageously, utilizing a non-target gas allows the detector testing system 100 to test cross sensitivity of the gas detector 200 to gases other than the target gas.

The detector testing system 100 may also be configured to test a responsiveness of the gas detector 200 to a target gas at various temperatures and humidity levels. The detector testing system 100 may include environmental controls 510 configured to adjust the environmental conditions within the testing chamber 110 and environmental sensors 520 configured to detect the environmental conditions within the testing chamber 110. The environmental controls 510 may include but are not limited to a heater 510$a$ and a humidifier 510$b$. The environmental sensors 520 include but are not limited to a temperature sensor 520$a$ and a humidity sensor 520$b$. Advantageously, by including environmental controls 510 and environmental sensors 520, the detector testing system 100 could test accuracy of the gas detectors 200 at multiple other temperature or humidity conditions rather than at the one environmental condition that occurred during the test. The controller 502 of the detector testing system 100 would be configured to establish environmental testing conditions within the testing chamber 110 using the environmental controls 510 and the environmental sensors 520 prior to reading the gas detector 200 output and comparing it to the target gas composition. Advantageously, adjusting the temperature and the humidity within the testing chamber 110 could be used to test gas detectors 200 having multipoint calibrations over a range of temperature and humidity levels.

The detector testing system 100 may also include a display device 120 configured to display detector readings from the gas detector 200, the concentration of the target gas or non-target gas being detected by the gas detector 200 enclosed within the testing chamber 110, a temperature within the testing chamber 110, and humidity conditions within the testing chamber 110. The display device 120 may include detector readings such as whether the sensor within the gas detector 200 being tested passes the accuracy level required or not (e.g., pass or no pass), whether relays or other system-level mitigation mechanisms including in the gas detector 200, such as, for example, lights or switches are operating or operating correctly. The detector testing system 100 may also include different relay indicator lights 130 that may illuminate when different rely signals are activated by the gas detector 200 in response to a target gas or non-target gas. For example, when the gas detector 200 detects a target gas of a certain concentration then the gas detector 200 may produce a rely signal to the HVAC/R system 300 to perform a task (e.g., switches, fan on/off switches, activate an alarm, shut off the HVAC/R system, etc.) and the rely signal from the gas detector 200 will be communicated to the detector testing system 100 through the communication devices 114, 214 and a relay indicator light 130 may illuminate, and the results may be displayed in the display device 120.

Figure 3:
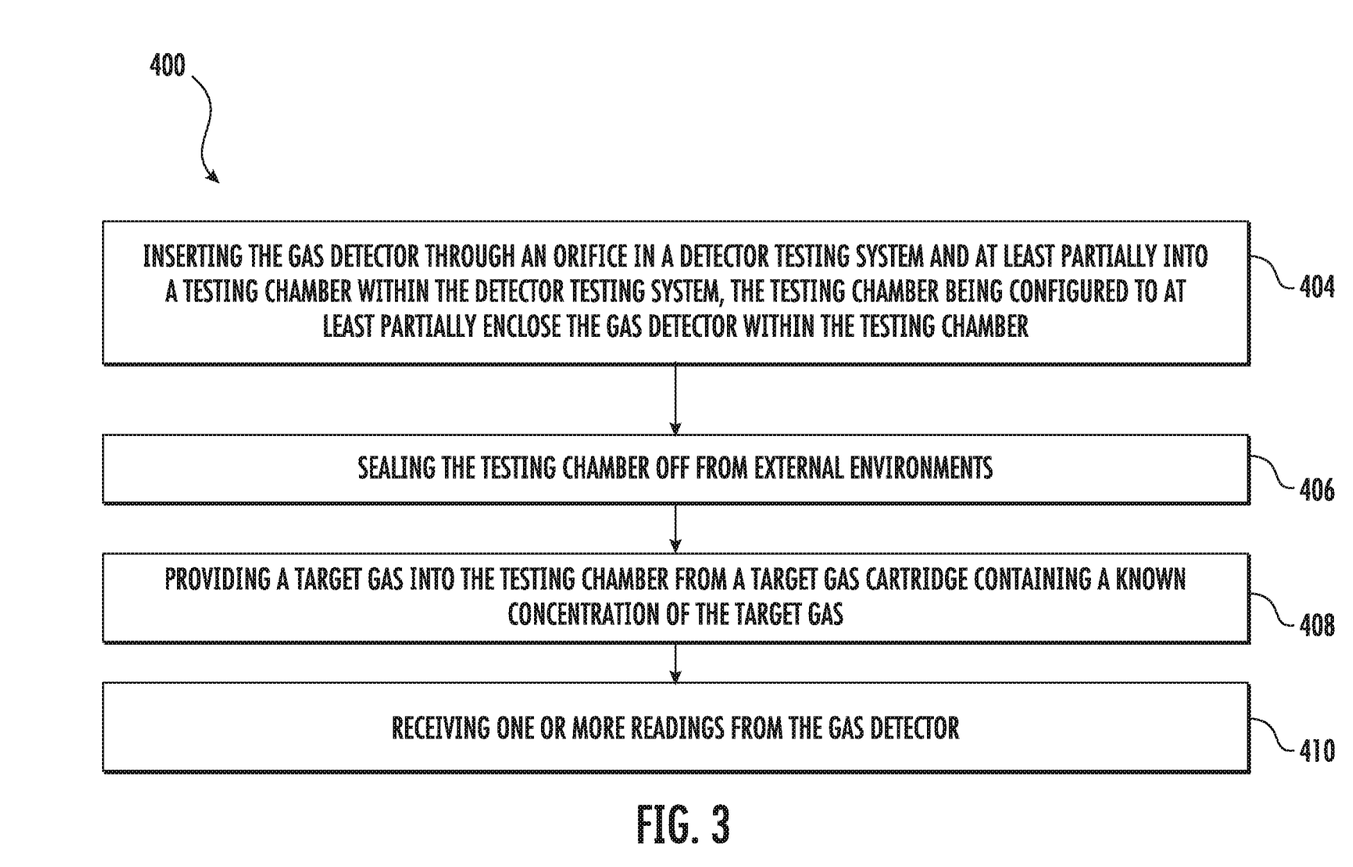
FIG. 3 is a flow diagram illustrating a method of testing a sensor for a heating, ventilation, and air conditioning or refrigeration system, according to an embodiment of the present disclosure.

Referring now to FIG. 3, with continued reference to FIGS. 1-2, a flow chart of a method 400 of testing the gas detector 200 for an HVAC/R system 300 is illustrated, in accordance with an embodiment of the present disclosure. In an embodiment, the method 400 is performed by the detector testing system 100. At block 404, the gas detector 200 is inserted through an orifice 118 in a detector testing system 100 and at least partially into a testing chamber 110 within the detector testing system 100. The testing chamber 110 being configured to at least partially enclose the gas detector 200 within the testing chamber 110. In an embodiment, the testing chamber 110 is configured to at least totally or completely enclose the gas detector 200 within the testing chamber 110.

At block 406, the testing chamber 110 is sealed off from external environments 210 external to the testing chamber 110 and/or the detector testing system 100. The testing chamber 110 may be sealed off from external environments 210 by: removing (e.g., detaching) the gas detector 200 from the HVAC/R system 300; inserting the gas detector 200 fully into the testing chamber 110; and closing a door 112 of the testing chamber 110. The door 112 is configured to seal against the orifice 118 and fully enclose the gas detector 200 within the testing chamber 110. The testing chamber 110 may also be sealed off from external environments 210 by: sealing the orifice 118 against a mounting surface 302 of the HVAC/R system 300 while the gas detector 200 remains attached to the mounting surface 302; and partially enclosing the gas detector 200 within the testing chamber 110.

At block 408, a target gas is provided into the testing chamber 110 from a target gas cartridge 150 containing a known concentration of the target gas. In an embodiment, the target gas is a refrigerant. In another embodiment, the target gas is a mildly flammable refrigerant. In another embodiment, the target gas is an A2 refrigerant, A2L refrigerant, or an A3 refrigerant. In another embodiment, the known concentration of the target gas within the target gas cartridge is a lower flammability limit of the target gas.

At block 410, one or more readings are received from the gas detector 200. The method 400 may further comprising displaying the one or more detector readings detected by the gas detector 200 either through the display device 120 or relay indicator lights 130. Additionally, the method 400 may further comprise: diluting the target gas to a lower flammability limit of the target gas prior to entering the testing chamber 110.

The method 400 may also comprise: detecting an environmental condition within the testing chamber 110 using an environmental sensor 520 adjusting the environmental condition within the testing chamber 110 using an environmental control 510. The method 400 may further comprise: receiving readings from the gas detector 200 and transmitting the readings to a cloud server 900. The method 400 may also further comprise: receiving readings from the gas detector 200; determining a recalibration of the gas detector 200 is required in response to the readings; and transmitting the calibration parameters or adjustments for recalibration of the gas detector to the gas detector 200.

While the above description has described the flow processes of FIG. 3 in a particular order, it should be appreciated that unless otherwise specifically required in the attached claims that the ordering of the steps may be varied.

Figure 4:
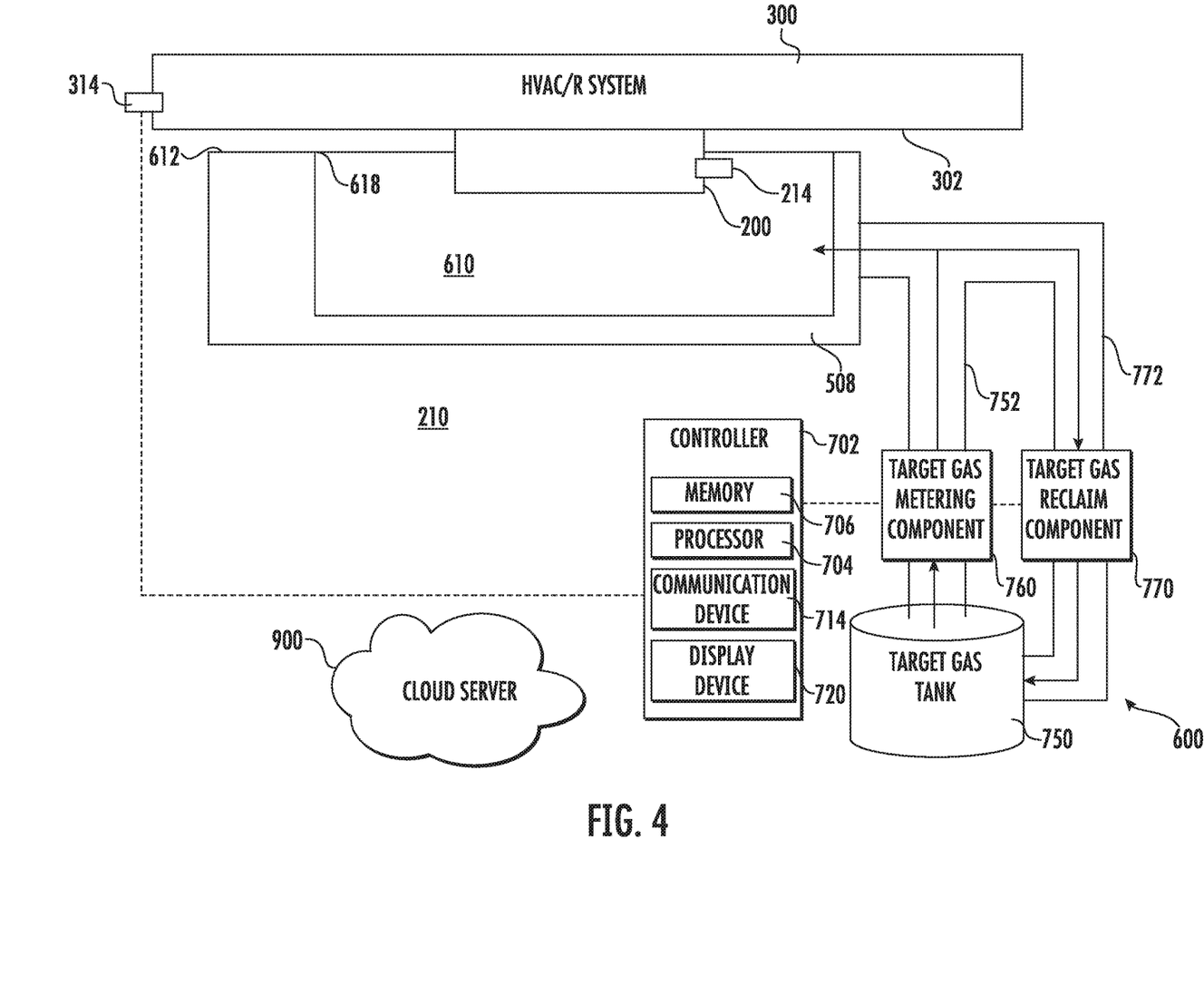
FIG. 4 illustrates a general system diagram of a detector testing system, in accordance with an embodiment of the disclosure.

FIG. 4 schematically illustrates a detector testing system 600 configured to test a gas detector 200 and an associated HVAC/R system 300. The gas detector 200 may contain various components that are tested by the detector testing system 600, such as for example gas sensors, diagnostic algorithms, and mitigation mechanisms such as lights, relays and switches. It should be appreciated that, although particular systems are separately defined in the schematic block diagrams, each or any of the systems may be otherwise combined or separated via hardware and/or software. The gas detector 200 is used in the HVAC/R system 300 to detect a target gas. In an embodiment, the target gas is a refrigerant. In an embodiment, the target gas is a flammable and/or a mildly flammable refrigerant. In one embodiment, a mildly flammable refrigerant may be defined as a refrigerant having a greater than 0.3 kg/m$^3$, a heat of combustion less than 19,000 kj/kg, and/or a burning velocity of less than 10 cm/s. In an embodiment, the mildly flammable refrigerant may be A2L refrigerant. An A2L refrigerant may include but is not limited to R32, R1234yf, R-1234ze(E), R134A, R454A, and R454B. In another embodiment, the target gas may be a higher flammability refrigerant, such as, for example an A3 refrigerant. In another embodiment, the target gas is an A2 refrigerant, A2L refrigerant, or an A3 refrigerant. An A2 refrigerant may include but is not limited to R-152a. An A3 refrigerant may include but is not limited to R-290 (Propane) and R-600a (isobutene).

The HVAC/R system 300 may be a commercial or residential stationary HVAC system or a transport or stationary refrigeration (R) system. The gas detector 200 may be utilized in operative association with a transport HVAC/R system, such as, for example, a refrigerated truck, a refrigerated trailer, or a refrigerated container. The gas detector 200 may also be utilized in operative association with a stationary HVAC/R system, such as, for example, refrigerated cabinets (e.g., self-serve refrigerated grocery cabinets with and without doors). In the transport refrigeration system or the commercial refrigeration system, the gas detector 200 may be used as part of a refrigeration control system to adjust environmental conditions of the perishable goods (e.g., cargo/stock/inventory) in order to control or influence the control of ventilation, humidity, air temperature, and/or contaminant scrubbing systems. In one embodiment, the gas detector 200 may be used to activate ventilation to lower the target gas concentration around the gas detector 200, or to alert personnel to the presence of the target gas, or potential damage to property or perishable goods. In another embodiment, the gas detector 200 may be utilized independent of a corresponding refrigeration system or commercial refrigeration system to alert personnel to potential damage to perishable goods, alert personnel to the presence of the target gas, and/or to increase or decrease ventilation rates.

The detector testing system 600 may be separate and apart from the gas detector 200 and may be utilized to test the gas detector 200 periodically or intermittently, as required. The detector testing system 600 may be brought onsite to test the gas detector 200. The detector testing system 600 may be brought to the HVAC/R system 300 to test the gas detector 200 while remaining installed in the HVAC/R system 300, as described herein.

The detector testing system 600 includes a testing cup 608 with a testing chamber 610 capable of partially enclosing the gas detector 200. The testing chamber 610 originates on a cup mounting surface 612 of the testing cup 608 and extends into the testing cup 608, as illustrated in FIG. 4.

In the embodiment illustrated in FIG. 4, the gas detector 200 is not removed from a mounting surface 302 of the HVAC/R system 300 but rather gas detector 200 is tested within the testing chamber 610 of the testing cup 608 while still being mounted to the mounting surface 302. As shown in FIG. 4, the gas detector 200 is inserted into an orifice 618 of the detector testing system 600. The orifice 618 opens up into the testing chamber 610. The cup mounting surface 612 is configured to seal against the mounting surface 302 of the HVAC/R system 300, while the testing chamber 610 encloses the gas detector 200. The cup mounting surface 612 sealing against the mounting surface 302 of the HVAC/R system 300 environmentally seals (i.e., isolates) the gas detector 200 within the testing chamber 610 and prevents gas leakage between the testing chamber 610 and an external environment 210 outside of the testing chamber 610.

When the gas detector 200 is sealed within the testing chamber 610, the detector testing system 600 is configured to emit a known concentration of the target gas into the testing chamber 610 to test a state of health of the gas detector 200 and a response of the HVAC/R system 300.

The detector testing system 600 may be in wired and/or wireless communication with the HVAC/R system 300 when the gas detector 200 is located within the testing chamber 610 to response data of the HVAC/R system 300. The detector testing system 600 may include a communication device 714 and the HVAC/R system 300 may include a communication device 314. In one embodiment, the communication device 314 of the HVAC/R system 300 may be hardwired to the communication device 714 of the detector testing system 600 through a removable connecting wire (not shown). In another embodiment, the communication device 314 of the HVAC/R system 300 may be in wireless communication with the communication device 714 of the detector testing system 600 through a short-range wireless transmissions, such as, for example, Bluetooth, Wi-Fi, Infrared, etc. Alternatively, there may be no communication between the detector testing system 600 and the HVAC/R system 300, a technician may verify a response of the HVAC/R system 300 to testing by the detector system testing system 600.

In one embodiment, a memory 706 of a controller 702 of the detector testing system 600 or any other memory device within the detector testing system 600 may be utilized to locally store testing data, including, but not limited to, building name, building number, room number, station number, time, test number, target gas name, target gas concentration, detector name, detector location, detector baseline, readings from the gas detector 200, detector response as function of time, the known concentration of the target gas within the target gas tank 750, the concentration of target gas delivered into the testing chamber 610, the humidity within the testing chamber 610, and the temperature within the testing chamber 610, and the like. In an embodiment, the controller 702 is configured to dispense a correct quantity of target gas for testing.

In one embodiment, the controller 702 of the detector testing system 600 may be configured to locally analyze the testing data, determine a pass or fail decision for the gas detector 200, and display the pass or fail decision back on the detector testing system 600. In another embodiment, the communication device 314 may be in wireless communication with a cloud server 900 through a wireless transmissions, such as, for example, Bluetooth, Wi-Fi, Infrared, cellular, satellite, or other network communication. The communication device 314 may be configured to transmit the testing data to the cloud server 900. The cloud server 900 may be configured to analyze the testing data, determine a pass or fail decision for the gas detector 200, and transmit the pass or fail decision back to the detector testing system 600 for local display. Testing data may be downloaded from the HVAC/R system 300 to the controller 702 or any other computing device for analysis.

In addition to determining a pass or fail, the controller 702 and/or the cloud server 900 may alternatively determine that the gas detector 200 needs to be recalibrated using the detector testing system 600. The communication device 114 of the detector testing system 100 may be in wireless communication with the communication device 214 of the gas detector 200 through a short-range wireless transmissions, such as, for example, Bluetooth, Wi-Fi, Infrared, etc. The communication device 114 of the detector testing system 100 may be in wired communication with the communication device 214 of the gas detector 200 through a USB cable, Ethernet, fiber-optics, etc. Through the communication devices 714, 214, the detector testing system 600 may be able to pass to the gas detector 200 calibration parameters or adjustments thereto for recalibration of the gas detector 200, which may be an automatic process. For example, once connected with the gas detector 200, the detector testing system 600 can pair with the gas detector 200 to start a calibration test where it delivers a known concentration of target gas into the testing chamber 610. Upon receiving the readings from the gas detector 200 in response to the target gas then the detector testing system 600 can send updated calibration parameters to the gas detector 200 and then rerun the test to confirm that the gas detector 200 has been successfully recalibrated.

The controller 702 may be configured to control entry of the target gas into the testing chamber 610 using a target gas metering component 760 or removal of the target gas from the testing chamber 610 using a target gas reclaim component 770. The controller 702 may be an electronic controller including a processor 704 and an associated memory 706 comprising computer-executable instructions that, when executed by the processor 704, cause the processor 704 to perform various operations. The processor 704 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 706 may be but is not limited to a random access memory (RAM), read only memory (ROM), or other electronic, optical, magnetic or any other computer readable medium.

The detector testing system 600 may also include a target gas delivery hose 752 fluidly connected to the testing chamber 610. The target gas tank 750 may be fluidly connected to the testing chamber 610 through a target gas delivery hose 752. The target gas metering component 760 may be located within the target gas delivery hose 752 interposed between the testing chamber 610 and the target gas tank 750. The target gas metering component 760 may be a metering valve, solenoid valve, stepper motor valve or similar component known to one of skill in the art. The target gas metering component 760 may adjust or meter how much of the target gas is delivered from the target gas tank 750 to the testing chamber 610. In one example, the target gas metering performed by the target gas metering component 760 may be done with a controller that opens a solenoid valve for a specific time, which is correlated to a quantity of refrigerant. In another example, the target gas metering performed by the target gas metering component 760 may be done by opening a stepper motor valve, measuring the flow rate with a flow-meter, and correlating that the flow rate to a quantity of refrigerant.

The target gas delivery hose 752 is configured to deliver the target gas into the testing chamber 610. The target gas tank 750 contains a known concentration of the target gas, such as, for example, 0%, 10%, 20%, 30%, 40%, 50%, 60%, 70%, 80%, 90%, 100%, or any concentration therebetween. In one embodiment, the target gas tank 750 may contain a known concentration of the target gas equal to about 100%. The detector testing system 600 includes target gas metering component 760 to adjust flow of the target gas from the target gas tank 750 into the testing chamber 610.

The detector testing system 600 may also include a target gas return hose 772 fluidly connected to the testing chamber 610. The target gas tank 750 may be fluidly connected to the testing chamber 610 through a target gas return hose 772. A target gas reclaim component 770 may be located within the target gas return hose 772 interposed between the testing chamber 610 and the target gas tank 750. The target gas reclaim component 770 may be a valve, a pump, a hermetic pump rated for flammable refrigerant, or any similar device known to one of skill in the art. The target gas reclaim component 770 may be configured to pump the target gas from the testing chamber 610 to the target gas tank 750 through the target gas return hose 772 once testing is completed. The pressure of the testing chamber 610 will be measured and pumped down to 0 psig.

The detector testing system 600 may also include a display device 720 configured to display response data of the HVAC/R system 300. The response data may indicate whether the HVAC/R system 300 has performed (or is performing) an isolation and pump down procedure following the introduction of the target gas into the testing chamber 610. The display device 720 may be controlled with a computing program, such as, for example, Vissim or MATLAB. The display device 720 may be a computer monitor or one or more lights with different meanings (e.g., red=test failed; green=test passed).

Figure 5:
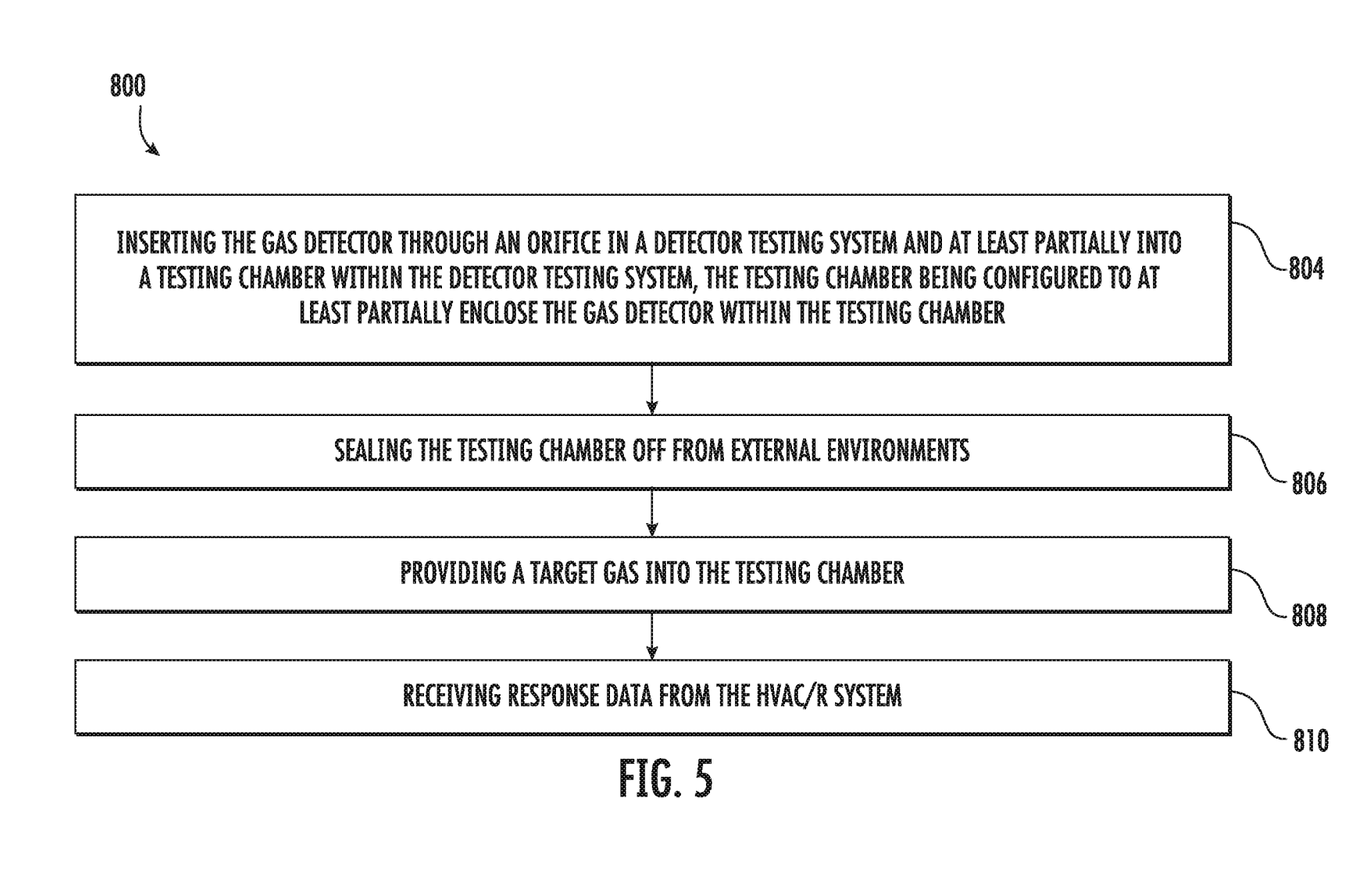
FIG. 5 is a flow diagram illustrating a method of testing a sensor for a heating, ventilation, and air conditioning or refrigeration system, according to an embodiment of the present disclosure.

Referring now to FIG. 5, with continued reference to FIG. 4, a flow chart of a method 800 of testing the gas detector 200 for an HVAC/R system 300 is illustrated, in accordance with an embodiment of the present disclosure. The method 800 may indicate a pass or fail of a safety system test. In an embodiment, the method 800 is performed by the detector testing system 600. At block 804, the gas detector 200 is inserted through an orifice 618 in a detector testing system 600 and at least partially into a testing chamber 610 within the detector testing system 600. The testing chamber 610 being configured to at least partially enclose the gas detector 200 within the testing chamber 610. In an embodiment, the testing chamber 610 is configured to at least totally or completely enclose the gas detector 200 within the testing chamber 610.

At block 806, the testing chamber 610 is sealed off from external environments 210 external to the testing chamber 610. The testing chamber 610 may be sealed off from external environments by sealing the cup mounting surface 612 against a mounting surface 302 of the HVAC/R system 300 while the gas detector 200 remains attached to the mounting surface 302; and partially enclosing the gas detector 200 within the testing chamber 610.

At block 808, a target gas is provided into the testing chamber 610 from a target gas tank 750 containing a known concentration of the target gas. In an embodiment, the target gas is a refrigerant. In another embodiment, the target gas is a mildly flammable refrigerant. In another embodiment, the target gas is an A2 refrigerant, A2L refrigerant, or an A3 refrigerant. In another embodiment, the known concentration of the target gas within the target gas cartridge is a lower flammability limit of the target gas.

At block 810, response data is received from the HVAC/R system 300. The response data may indicate whether the HVAC/R system 300 has performed or is performing an isolation and pump down procedure following the introduction of the target gas into the testing chamber 610. If the HVAC/R system 300 has performed (or is performing) an isolation and pump down procedure following the introduction of the target gas then the HVAC/R system 300 is considered to have passed a safety system test. If the HVAC/R system 300 has not performed (or is not performing) an isolation and pump down procedure following the introduction of the target gas then the HVAC/R system 300 is considered to have failed the safety system test.

The method 800 may further comprise that the target gas is transported from the testing chamber 610 to a target gas tank 750. The target gas may be transported from the testing chamber 610 to a target gas tank 750 using the target gas reclaim component 770 through the target gas return hose 772.

While the above description has described the flow processes of FIG. 5 in a particular order, it should be appreciated that unless otherwise specifically required in the attached claims that the ordering of the steps may be varied.

As described above, embodiments can be in the form of processor-implemented processes and devices for practicing those processes, such as processor. Embodiments can also be in the form of computer program code (e.g., computer program product) containing instructions embodied in tangible media, such as floppy diskettes, CD ROMs, hard drives, or any other non-transitory computer readable medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an device for practicing the exemplary embodiments. When implemented on a general-purpose microprocessor, the computer program code segments configure the microprocessor to create specific logic circuits.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A detector testing system for testing a gas detector used in a heating, ventilation, and air conditioning, or refrigeration (HVAC\R) system, the detector testing system comprising:
   a testing chamber configured to receive the gas detector through an orifice in the detector testing system, the testing chamber being configured to at least partially enclose the gas detector within the testing chamber;
   a receiving port fluidly connected to the testing chamber; and
   a target gas cartridge fluidly connected to the receiving port, wherein the target gas cartridge contains a known concentration of a target gas,
   wherein the target gas is a refrigerant;
   wherein the known concentration of the target gas within the target gas cartridge is a lower flammability limit of the target gas or wherein the target gas within the target gas cartridge is diluted to a lower flammability limit of the target gas prior to the target gas entering the testing chamber;
   wherein the receiving port is configured to deliver the target gas to the testing chamber;
   wherein the orifice is configured to seal against a mounting surface of the HVAC/R system and enclose the gas detector, which is mounted to the mounting surface of the HVAC/R system, within the testing chamber isolating the gas detector within the testing chamber and preventing gas leakage between the testing chamber and an external environment outside of the testing chamber.

2. The detector testing system of claim 1, further comprising:
   a communication device in electronic communication with a communication device of the gas detector.

3. The detector testing system of claim 1, further comprising:
   a display device configured to display detector readings detected by the gas detector.

4. The detector testing system of claim 1, wherein the target gas is a mildly flammable refrigerant.

5. The detector testing system of claim 1, wherein the target gas is an A2 refrigerant, A2L refrigerant, or an A3 refrigerant.

6. The detector testing system of claim 1, further comprising:
   an environmental control configured to adjust an environmental conditions within the testing chamber; and
   an environmental sensor configured to detect the environmental condition within the testing chamber.

7. The detector testing system of claim 6, wherein the environmental condition includes at least one of a temperature and a humidity level.

8. The detector testing system of claim 1, further comprising:
   a communication device in electronic communication with a communication device of the gas detector, wherein the communication device is configured to received readings detected by the gas detector and transmit the readings to a cloud server.

9. The detector testing system of claim 1, further comprising:
   a communication device in electronic communication with a communication device of the gas detector, wherein the communication device is configured to communicate with the gas detector for recalibration of the gas detector.

* * * * *